(12) United States Patent
Mohar

(10) Patent No.: US 7,538,246 B2
(45) Date of Patent: May 26, 2009

(54) SYNTHESIS OF OPTICALLY PURE(R)-5-(2-AMYNOPROPYL)-2-METHOXYBENZENESULPHONAMIDE

(75) Inventor: Barbara Mohar, Grosuplje (SI)

(73) Assignee: Lek Pharmaceuticals d.d., Ljubljana (SI)

( * ) Notice: Subject to any disclaimer, the term of this patent is extended or adjusted under 35 U.S.C. 154(b) by 0 days.

(21) Appl. No.: 10/584,369

(22) PCT Filed: Dec. 27, 2004

(86) PCT No.: PCT/SI2004/000046

§ 371 (c)(1),
(2), (4) Date: Nov. 13, 2006

(87) PCT Pub. No.: WO2005/063701

PCT Pub. Date: Jul. 14, 2005

(65) Prior Publication Data

US 2007/0155989 A1    Jul. 5, 2007

(30) Foreign Application Priority Data

Dec. 29, 2003  (SI)  ................................. 200300320

(51) Int. Cl.
*C07C 303/36*  (2006.01)
*C07C 309/29*  (2006.01)
(52) U.S. Cl. ....................................................... 564/86
(58) Field of Classification Search ...................... None
See application file for complete search history.

(56) References Cited

U.S. PATENT DOCUMENTS 3,860,647 A * 1/1975 Colella et al. .................. 564/86

FOREIGN PATENT DOCUMENTS

WO    WO 03/035608    5/2003

OTHER PUBLICATIONS

Database CAPLUS on STN, Acc. No. 1993:21983, Sakurai et al., Chemical & Pharmaceutical Bulletin (1992), 40(6), p. 1443-1451 (abstract).*
Meiling Qi et al.: Determination of the enantiomers of tamsulosin hydrochloride and its synthetic intermediates by Chiral liquid chromatography: Chromatographia, vol. 59, No. 3/4, Feb. 3, 2004, pp. 251-254, XP009048997.

* cited by examiner

*Primary Examiner*—Brian J Davis
(74) *Attorney, Agent, or Firm*—Luedeka, Neely & Graham, P.C.

(57) ABSTRACT

The present invention relates to a new process for the preparation of optically pure(R)-5-(2-aminopropyl)-2-methoxybenzenesulphonamide, which is an intermediate in the synthesis of tamsulosin.

21 Claims, No Drawings

SYNTHESIS OF OPTICALLY PURE(R)-5-(2-AMYNOPROPYL)-2-METHOXYBENZENESULPHONAMIDE

CLAIM OF PRIORITY

The present application claims priority to PCT Application No. PCT/SI2004/000046 filed on Dec. 27, 2004, in the name of LEK Pharmaceuticals D.D., which claims priority to Slovenian Patent Application No. P-200300320 filed in Slovenia on Dec. 29, 2003.

FIELD OF THE INVENTION

The present invention relates to a new process for the synthesis of (R)-5-(2-aminopropyl)-2-methoxybenzenesulphonamide starting from D-alanine and methoxybenzene via a Friedel-Crafts reaction. More particularly, the invention relates to a new process for the preparation of tamsulosin.

BACKGROUND OF THE INVENTION

Tamsulosin is a pharmaceutical active substance from the group of antagonists of $\alpha_1$-adrenergic receptors, which are used for the treatment of functional disorders of the prostate. Tamsulosin is chemically (R)-5-(2-((2-(2-ethoxyphenoxy)ethyl)amino)propyl)-2-methoxybenzenesulphonamide (formula 1) and belongs to the groups of benzensulphonamides and sulphamoyl phenethylamines.

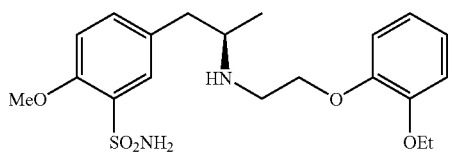

Tamsulosin is commercially marketed in a form of the hydrochloride of pure (R)-enantiomer and is used for the treatment of benign prostatic hyperplasia. According to the invention the term "tamsulosin" means the compound of formula (1) in a form of the hydrochloride salt whereas the compound in a non-salt form is named the tamsulosin base.

There is a constant need for the preparation of pharmaceutical active substances with a quality suitable for incorporation into a final medical product in technologically as simple and economical way as possible. Tamsulosin is a chiral molecule and its (R)-enantiomer is used as a therapeutic active substance. Providing an optically pure compound with a minimal portion of the undesired (S)-isomer is a serious technical problem being relatively difficult to solve because enantiomers cannot be separated by conventional chemical methods and separations.

Tamsulosin may be prepared according to the basic patent EP 34432 in which examples disclose first the preparation of a racemate which is further purified by column chromatography on a chiral matrix to obtain enantiomers.

Patent applications WO 03/37850 and WO 03/37851 disclose an alternative preparation of tamsulosin via synthesis of the crystalline racemic tamsulosin base which should be purified with expensive camphor-5-sulphonic acid. In WO 03/37850 such separation of final racemic tamsulosin base is explicitly reported, however, in the last step there is always a risk that chiral separation would not be complete and a product with a greater amount of the opposite enantiomer would be obtained.

In CZ 290.708 a process for the separation of racemic tamsulosin by using an acid is disclosed.

To avoid such separations, the optically pure (R)-5-(2-aminopropyl)-2-methoxybenzenesulphonamide (2) should be prepared.

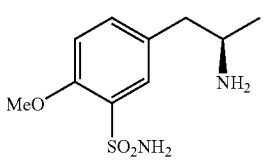

(R)-5-(2-aminopropyl)-2-methoxybenzenesulphonamide (2) is known in the art as a key intermediate in the synthesis of tamsulosin. Processes for the synthesis of (R)-5-(2-aminopropyl)-2-methoxybenzenesulphonamide (2) have already been reported in the prior art. For example:

U.S. Pat. No. 5,447,958 discloses the synthesis of the compound (2). The starting product is (−)-2-(p-methoxyphenyl)-1-methylethylamine) whereby the synthesis thereof is not disclosed.

In EP 380144 the synthesis of the compound (2) starting with reductive amination of 5-acetonyl-2-methoxybenzenesulphonamide with R(+)α-methyl benzylamine, followed by hydrogenesis. Synthesis of 5-acetonyl-2-methoxy benzenesulphonamide is not disclosed.

In CA 1,282,077 among other processes also the synthesis of the compound (2) is disclosed starting from (R)(−)-2-(p-methoxyphenyl)-1-methylethylamine without indicating the process of preparation of the latter.

It would be therefore desirable to develop alternative processes for a more straightforward preparation of (R)-5-(2-aminopropyl)-2-methoxybenzene sulphonamide, which does not require the optical resolution of intermediates, allowing the industrial preparation of this product to be simplified and, therewith, the production costs to be reduced.

SUMMARY OF THE INVENTION

The present invention provides a new and straightforward process for the preparation of (R)-5-(2-aminopropyl)-2-methoxybenzenesulphonamide starting from D-alanine and methoxybenzene via a Friedel-Crafts reaction.

The process according to the present invention avoids the several drawbacks associated with the aforementioned processes: sophisticated synthesis, expensive reagents and starting materials, optical resolution of intermediates and/or enantiomer separation of tamsulosin after the final step of the process.

DETAILED DESCRIPTION OF THE INVENTION

The Friedel-Crafts reaction is known in the art. For example Nordlander et al. describe that chiral N-trifluoroacetyl substituted amino acids derivatives undergo Friedel-Crafts reaction with benzene and methoxybenzene (J. Org. Chem., 50 (1985), 3481). Moreover the Friedel-Crafts reaction of aromatics with N-protected alanyl chloride has been reported as a method for the preparation of homochiral cathinones (M. Osorio-Olivares et al., Tetrahedron: Asymmetry, 14 (2003), 1473). However, the Friedel-Crafts reaction of D-alanine and methoxybenzene has never been disclosed in the prior art.

It has been surprisingly found that using a minimal number of steps, it is possible to synthesise (R)-5-(2-aminopropyl)-2-methoxybenzenesulphonamide from D-alanine and methoxybenzene by using the reactions wherein no racemization of the asymmetric centre occurs. In this manner, (R)-5-(2-aminopropyl)-2-methoxybenzenesulphonamide may be prepared with an optical and chemical purity suitable for preparation of tamsulosin for any pharmaceutical use.

The first embodiment of the present invention is related to a process for the preparation of (R)-5-(2-aminopropyl)-2-methoxybenzene sulphonamide starting from D-alanine and methoxybenzene via a Friedel-Crafts reaction.

Preferably, the present invention is related to a process for preparing (R)-5-(2-aminopropyl)-2-methoxybenzene sulphonamide comprising the following steps:

a) protection of the amino group of D-alanine,
b) reaction of the obtained N-protected D-alanine with methoxybenzene to form the corresponding 4'-methoxy-2-amino protected propiophenone,
c) complete reduction of the oxo-group of the formed 4'-methoxy-2-amino protected propiophenone to form the corresponding amino-protected 1-(4-methoxyphenyl)propane-2-amine,
d) chlorosulphonation of the obtained amino-protected 1-(4-methoxyphenyl) propane-2-amine and subsequent ammonolysis of the formed chlorosulphonyl group and
e) deprotecton of the amino group.

D-alanine is a simple raw material, commercially available in large quantities, at a moderate price and with a high optical purity.

The process according to the present invention allows the synthesis of (R)-5-(2-aminopropyl)-2-methoxybenzenesulphonamide (2) by using as simple raw materials as are D-alanine and methoxybenzene without racemisation. Thus the process according to the present invention is a straightforward one, does not require any specific conditions to ensure an enantioselective synthesis and/or separation of enantiomers whereby there exists a risk that said would be incomplete which would result in a product having a too low enantiomeric excess (=e.e.) and in an optically impure product, respectively. It is necessary, therefore, to choose reactions wherein no racemization on the asymmetric carbon atom occurs, thus resulting in an optically pure product which may be used for synthesis of the pharmaceutical active substance tamsulosin.

According to step (a), D-alanine is protected with any amino protecting group (X) well known and commonly used in peptidic chemistry provided that said protecting group will not allow racemization of the D-alanine asymmetric center via the conversion into an oxazolidinone in a subsequent step of the process (Scheme 1). For example, suitable amino protecting groups are selected from the group consisting of trifluoroacetyl; alkyloxycarbonyl, such as t-butoxycarbonyl, benzyloxycarbonyl, fluorenylmethyloxycarbonyl; phthalimide. Preferred amino protecting group is the trifluoroacetyl group.

The amino protected D-alanine is then converted into an acid activated amino protected D-alanine with an acid activating reagent. Said acid activated group can be an acid chloride, anhydride or any other acid activated group well known in peptidic synthesis. For example, suitable acid activating reagents are selected from the group consisting of acid chloride or anhydride, preferably acid chlorides. More preferred acid activating reagents for the preparation of (R)-(N-trifluoroacetyl)propionyl chloride are oxalyl chloride and thionyl chloride. Most preferred is thionyl chloride.

The acid activated amino protected D-alanine may be isolated and as such charged into the next reaction step (b) or may be transferred into the further reaction step (b) in solution without isolation. Methylene chloride is a solvent suitable for both acid activated amino protected D-alanine formation and Friedel-Crafts reaction, so that the formed acid activated amino protected D-alanine can be added directly to the next step (Friedel-Crafts reaction).

Methoxybenzene, also known as anisole, is commercially available. Methoxybenzene is sufficiently activated for electrophilic substitutions of a Friedel-Crafts type to enable a smooth reaction with the acid activated amino protected D-alanine. Preferably a Lewis acid is added during the Friedel-Crafts reaction according to step (b). A suitable Lewis acid is selected from the group consisting of aluminium, iron (III), tin (IV), bismuth, boron compounds and salts of other transition metals or lanthanides.

In the Friedel-Crafts reaction between anisole and the acid activated amino protected D-alanine, substitution may occur in the position para (4 in view of the methoxy group) or ortho (2 in view of the methoxy group) with regard to the activation for electrophilic substitutions. We have found that the para position is more favoured in this reaction. The ratio between the ortho- and the para-substituted product depends on the reaction conditions, solvents and, above all, on the type of Lewis acid. The portion of the ortho-substituted product in the entire amount of substituted products is between 15 and 30% when $AlCl_3$, $FeCl_3$, $TiCl_4$ or bismuth triphlate is used as a Lewis acid with or without the addition of a co-ligand, nitromethane. The reaction is carried out at temperatures from about 0 to about 45° C., preferably at about 20-25° C. The optimal yield was obtained by using aluminium chloride at room temperature whereby the term optimal means that the range of conversion, the portion of the para-substituted product and absence of racemization on the asymmetric carbon atom are taken into consideration.

The oxo-group of the propiophenone intermediate obtained from the Friedel-Crafts reaction can be reduced, according to step (c), by means of complete reduction to the methylene group. Preferred reduction agents are silicon hydrides, either as polyalkylhydroxysiloxanes or alkylsilanes. Preferably triethylsilane is used. N-protected (R)-(4-methoxyphenyl)propane-2-amine is obtained from step (c).

According to step (d), the N-protected (R)-(4-methoxyphenyl)propane-2-amine is chlorosulphonated with chlorosulphonic acid wherein electrophilic substitution is predominantly directed to position 2 in view of the methoxy group. Chlorosulphonation according to step (d) may be carried out in the reagent itself or it may be diluted. Thionyl chloride is preferably used for said reaction. The obtained sulphonyl chloride is subsequently converted into sulphonamide with ammonia, preferably with an aqueous ammonia solution.

The desired compound, (R)-5-(2-aminopropyl)-2-methoxybenzene sulphonamide, is obtained by deprotection of the amino protective group according to step (e). This deprotection can be carried out by any conventional technique well known in the art, such as T. W. Greene and P. G. Wuts in "Protective groups in organic synthesis", $2^{nd}$ Edition. For example, the removal of the trifluoroacetyl group can be carried out either in an acidic medium, e.g. diluted hydrochloric acid, or in a basic medium, e.g. hydrolysis with potassium carbonate in alcohol, preferably in methanol, more preferably in aqueous methanol.

(R)-5-(2-aminopropyl)-2-methoxybenzenesulphonamide obtained according to the present invention is the suitable raw material for production of tamsulosin as not more than 0.3% of the undesired (S)-isomer can be detected by using HPLC with a chiral column. Using the known process, tamsulosin base is converted to tamsulosin hydrochloride which is suitable for any pharmaceutical use.

A preferred process according to the invention giving excellent results for the synthesis of (R)-5-(2-aminopropyl)-2-methoxybenzenesulphonamide is shown in Scheme 2.

In a specific embodiment, the process according to the present invention comprises an additional step wherein tamsulosin is obtained after the o-ethoxy phenoxyethylation of the amino group of (R)-5-(2-aminopropyl)-2-methoxy benzenesulphonamide. This subsequent step is has been disclosed in the art, such as EP 380,144 or U.S. Pat. No. 5,447,958. Tamsulosin hydrochloride can be obtained subsequently by treating tamsulosin with ethanolic HCl.

The present invention is also related to (R)-5-(2-aminopropyl)-2-methoxy-benzenesulphonamide prepared according to the preparation process as previously disclosed.

The present invention is also related to tamsulosin or tamsulosin hydrochloride prepared from (R)-5-(2-aminopropyl)-2-methoxybenzenesulphonamide obtained according to the preparation process as previously disclosed.

A still further object of the present invention is related to the use of (R)-5-(2-aminopropyl)-2-methoxybenzenesulphonamide for the synthesis of tamsulosin, characterised in that (R)-5-(2-aminopropyl)-2-methoxybenzenesulphonamide is prepared according to the preparation process as previously disclosed.

A further object of the present invention is related to the following new intermediate derivatives:
(R)-1-(4-methoxy-3-sulphamoylphenyl)-2-trifluoroacetylaminopropane,
(R)-1-(4-methoxy-3-sulphamoylphenyl)-2-trifluoroacetylamino-1-propanone.

Another object of the present invention is related to a pharmaceutical formulation comprising tamsulosin or tamsulosin hydrochloride wherein tamsulosin is prepared from (R)-5-(2-aminopropyl)-2-methoxybenzene sulphonamide prepared according to the preparation process as previously disclosed.

EXAMPLES

The present invention is more particularly described and explained by the following examples. It is to be understood, however, that the present invention is not limited to these examples and various changes and modifications may be made without departing from the scope of the present invention.

Example 1

Synthesis of N-(trifluoroacetyl)-D-alanine

To the mixture of D-alanine (20.00 g; 0.224 mol) and triethylamine (31.3 ml; 0.224 mol) in absolute methanol (100 ml), ethyl trifluoroacetate (33.4 ml; 0.280 mol) is added and stirred at room temperature to homogenise the mixture (approx. 1 day). The solution is concentrated on a rotavapor (35° C.; 16 mmHg) and then dissolved in the mixture THF/water (1:1; 140 ml). Acidic ion exchanger Dowex 50W-X8 (100 g) is added, stirred for 10 minutes, filtered and concentrated again on a rotavapor (35° C.; 16 mmHg). The residue is sublimed (80° C.; 0.05 mmHg). The pure product in the form of colourless crystals is obtained (33.50 g; 80.8%).

Example 2

Synthesis of (R)-N-(trifluoroacetyl)-α-amino-4'-methoxypropiophenone

To the mixture of N-(trifluoroacetyl)-D-alanine (10.00 g; 0.054 mol) and pyridine (100 µl) in $CH_2Cl_2$ (100 ml), thionyl chloride (4.1 ml; 0.057 mol) is added dropwise at room temperature and then stirred for 7 hours at 45° C. Anisole (7.0 ml; 0.065 mol) is added and the solution is cooled on an ice-bath. $AlCl_3$ (7.92 g; 0.059 mol) is added in portions and stirred at room temperature for 36 hours. The reaction is terminated with the addition of cold 1M HCl (150 ml) and ice (100 ml). The organic phase is washed with 1M HCl (2×100 ml), water (2×100 ml), saturated $NaHCO_3$ solution (2×100 ml), dried over anhydrous sodium sulphate and concentrated. Heptane (35 ml) is added to the residue while stirring. The formed para-product is filtered off and washed with heptane (2×25 ml). White needle-like crystals are obtained: 4.80 g (32,3% yield); >99% e.e.; $[\alpha]_{579}^{23}$ −40.4; $[\alpha]_{546}^{23}$ −47.0 (c 1.0; MeOH), ortho-product assay 1-2%, melting point 110-114° C., $^1$H-NMR ($CDCl_3$): 1.52 (d, 3H, $CH_3$; J=7.2 Hz); 3.91 (s, 3H, MeO); 5.47 (m, 1H, CH); 7.00 (m, 2H, H-2.6); 7.64 (broad s, 1H, $NHCOCF_3$); 7.97 (m, 2H, H-3.5).

An additional portion of crystals is formed from the filtrate which are filtered off and washed with petroleum ether (2×15 ml): 1.4 g; ortho:para=1:1.

Example 3

Synthesis of (R)-N-(trifluoroacetyl)-α-amino-4'-methoxypropiophenone

To the cooled (0° C.) mixture of D-N-(trifluoroacetyl)alanine (1.00 g; 5.4 mmol) and pyridine (1 drop) in $CH_2Cl_2$ (20 ml), oxalyl chloride (0.50 ml; 5.7 mmol) is added dropwise and then stirred for 2 hours at room temperature. Nitromethane (330 mg; 5.4 mmol) and anisole (0.7 ml; 6.5 mmol) are added and the solution is cooled on an ice-bath. $AlCl_3$ (0.79 g; 5.9 mol) is added in portions and stirred at room temperature for 36 hours. The reaction is terminated with the addition of cold 1M HCl (15 ml) and ice (10 ml). The organic phase is washed with 1M HCl (2×10 ml), water (2×10 ml), saturated $NaHCO_3$ solution (2×10 ml), dried over anhydrous sodium sulphate and evaporated. Petroleum ether (2.5 ml) is added to the residue while stirring. The formed para-product is filtered off and washed with petroleum ether (2×2.5 ml). White needle-like crystals are obtained: 330 mg, >99% e.e.

Example 4

Synthesis of (R)-N-(trifluoroacetyl)-α-amino-4'-methoxypropiophenone

To the mixture of D-N-(trifluoroacetyl)alanine (1.0 g; 5.4 mmol) and pyridine (5.0 µl) in $CH_2Cl_2$ (10 ml), thionyl chloride (0.41 ml; 5.7 mmol) is added dropwise at room temperature and then stirred for 5 hours at 45° C. Nitromethane (330 mg; 5.4 mmol) and anisole (0.7 ml; 6.5 mmol) are added and the solution is cooled on an ice-bath. $FeCl_3$ (0.96 g; 5.9 mol) is added in portions and stirred at room temperature for 24 hours. The reaction is terminated with the addition of cold 1M HCl (15 ml) and ice (10 ml). The organic phase is washed with 1M HCl (2×10 ml), water (2×10 ml), saturated $NaHCO_3$ solution (2×10 ml), dried over anhydrous sodium sulphate and evaporated. To the residue, petroleum ether (2.5 ml) is added while stirring. The formed para-product is filtered off and washed with petroleum ether (2×2.5 ml). White needle-like crystals are obtained: 405 mg, >99% e.e.

Example 5

Synthesis of (R)-N-(trifluoroacetyl)-α-amino-4'-methoxypropiophenone

To the mixture of D-N-(trifluoroacetyl)alanine (10.0 g; 0.054 mmol) and pyridine (50 µl) in $CH_2Cl_2$ (100 ml), thionyl chloride (4.1 ml; 0.057 mol) is added dropwise at room temperature and then stirred for 5 hours at 45° C. Anisole (7.0 ml; 0.065 mol) is added and the solution is cooled on an ice-bath. $TiCl_4$ (32.1 g; 0.135 mol) is added in portions and stirred at room temperature for 36 hours. The reaction is terminated with the addition of cold 1M HCl (150 ml) and ice (100 ml). The organic phase is washed with 1M HCl (2×100 ml), water (2×100 ml), saturated $NaHCO_3$ solution (2×100 ml), dried over anhydrous sodium sulphate and evaporated. Petroleum ether (25 ml) is added to the residue while stirring. The formed para-product is filtered off and washed with petroleum ether (2×25 ml). White needle-like crystals are obtained: 0.6 g, >99% e.e.

Example 6

Synthesis of (R)-2-(N-(trifluoroacetyl)amino)-1-(4'-methoxyphenyl)propane

To the mixture of (R)-2-N-(trifluoroacetyl)-α-amino-4'-methoxypropiophenone (7.5 g; 27.2 mmol) in $CF_3CO_2H$ (21 ml; 273 mmol), triethylsilane (13.5 ml; 81.8 mmol) is added dropwise and stirred at room temperature for 1 day. The mixture is then poured onto ice (40 ml) and neutralised with 4N NaOH. The product is extracted in EtOAc (3×20 ml), dried over $MgSO_4$, filtered and evaporated. The residue is washed with heptane (3×30 ml) and dried. White colourless crystals are obtained: 6.78 g; >99% e.e.; $[\alpha]_D^{23}$+15.0 (c 1.0; MeOH); melting point 100-102° C., $^1$H-NMR ($CDCl_3$): 1.21 (d, 3H, $CH_3$; J=6.6 Hz); 2.79 (m, 2H, $CH_2$); 3.80 (s, 3H, OMe); 4.25 (m, 1H, CH); 6.05 (broad s, 1H, $NHCOCF_3$); 6.86 (m, 2H, H-3.5); 7.08 (m, 2H, H-2.6).

Example 7

Synthesis of (R)-2-(N-(trifluoroacetyl)amino)-1-(4'-methoxy-3'-sulphamoyl)-phenylpropane To the cooled (−10° C.) solution of (R)-2-(N-(trifluoroacetyl)amino)-1-(4'-methoxy)phenylpropane (5.00 g; 19.1 mmol) in $SOCl_2$ (4.2 ml; 57.4 mmol), $ClSO_3H$ (2.5 ml; 38.2 mmol) is added dropwise. The mixture is heated slowly to 40° C. and stirred at the same temperature for 3 hours. A brown-red coloured viscous mixture is obtained, cooled to room temperature and added dropwise to the cooled (0° C.) 28% aqueous ammonia (30 ml) and acetone (15 ml). After the addition has been completed, the mixture is stirred for 10 minutes and then acetone is evaporated. The product in a form of a white precipitate is formed, filtered off, washed with water (2×20 ml), dried and then washed with i-$Pr_2O$ (40 ml): white powder; 6.13 g; 94% yield. $[\alpha]_{546}^{23}$−5.0 (c 1.0; MeOH); melting point 171-173° C., $^1$H-NMR (DMSO-$d_6$): 1.14 (d, 3H, $CH_3$; J=6.6 Hz); 2.76 (m, 2H, $CH_2$); 3.87 (s, 3H, OMe); 4.00 (m, 1H, CH); 7.01 (br s, 2H, $SO_2NH_2$); 7.12 (d, 1H, H-5; J=8.4 Hz); 7.38 (dd, 1H, H-6; J=8.4 and 2.1 Hz); 7.58 (d, 1H, H-2; J=2.1 Hz); 9.34 (broad d, 1H, $NHCOCF_3$; J=8.1 Hz).

Example 8

Synthesis of (R)-2-amino-1-(4'-methoxy-3'-sulphamoyl)phenylpropane $K_2CO_3$ (13 g; 94 mmol) and water (5 ml) are added to the solution of R-2-(N-(trifluoroacetyl)amino)-1-(4'-methoxy-3'-sulphamoyl)phenylpropane (4.00 g; 11.75 mmol) in MeOH (80 ml) The mixture is heated for 8 hours at the temperature of boiling and evaporated. Water (20 ml) is added to the residue and stirred overnight. The product in a form of the white precipitate is formed, filtered off, washed with water (2×5 ml) and dried; a slightly coloured white powder is obtained, 2.65 g; 94% yield, 97+% purity according to $^1$H-NMR. The product is recrystallised from i-PrOH (45 ml): a slightly coloured white powder is obtained; 2.55 g; 89% yield, >98% purity according to $^1$H-NMR, $[\alpha]_D^{23}$−17.8 (c 1.0, MeOH); melting point 168-170° C.; $^1$H-NMR (DMSO-$d_6$): 0.94 (d, 3H, $CH_3$; J=6.3 Hz); 2.51 (m, overlapped with DMSO, $CH_2$); 2.94 (m, 1H, CH); 3.87 (s, 3H, OMe); 7.11 (d, 1H, H-5; J=8.4 Hz); 7.36 (dd, 1H, H-6; J=8.4 and 2.0 Hz); 7.36 (d, 1H, H-2; J=2.0 Hz).

Example 9

Synthesis of 5-(2-(2-(2-ethoxyphenoxy)-ethylamino)-propyl)-2-methoxybenzene-sulphonamide Hydrochloride (Tamsulosin)

(R)-2-(N-(trifluoroacetyl)amino)-1-(4'-methoxy-3'-sulphamoyl)phenylpropane (10 g), 2-(o-ethoxyphenoxy)ethyl bromide (19 g) and MeOH (170 ml) are refluxed for 43 hours. MeOH is evaporated in vacuo on a rotavapor at 60° C. To the residue 170 ml of water, 130 ml of ethylacetate and during cooling and stirring 16 g of 50% NaOH are added. If both phases are not clear, NaOH is added until clarification is achieved. After separation of both phases, the aqueous phase is extracted with 2×100 ml of ethylacetate. The combined extracts are washed with 2×130 ml of water and evaporated in vacuo on a rotavapor at 60° C. The obtained crude tamsulosin base still contains much excessive 2-(2-ethoxyphenoxy)ethylbromide. It is dissolved in 100 ml of EtOH and during cooling and stirring, 7 ml of ethanolic HCl (approx. 300 mg of HCl/ml) is added. While cooling (0° C.) it is stirred for 4 hours and the formed crude tamsulosin in a form of hydrochloride was removed by centrifuging, washed with 20 ml of cold EtOH and dried in vacuo at 40° C. to give 7.0 g of the product.

Scheme 1

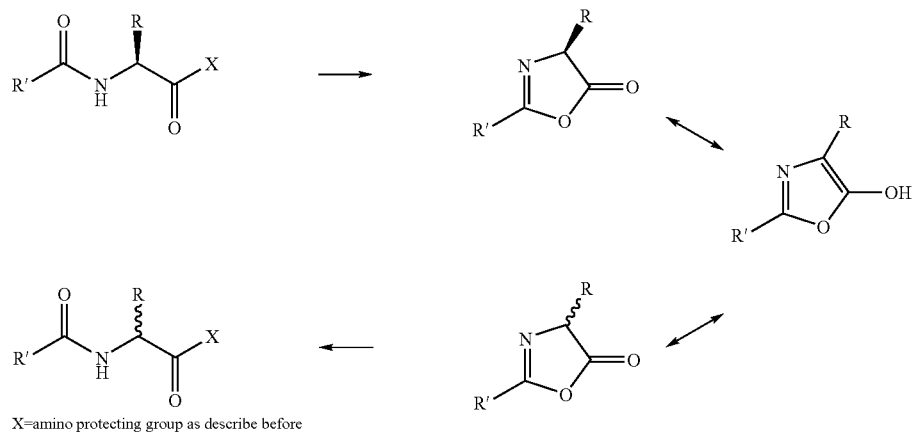

X=amino protecting group as describe before

Scheme 2

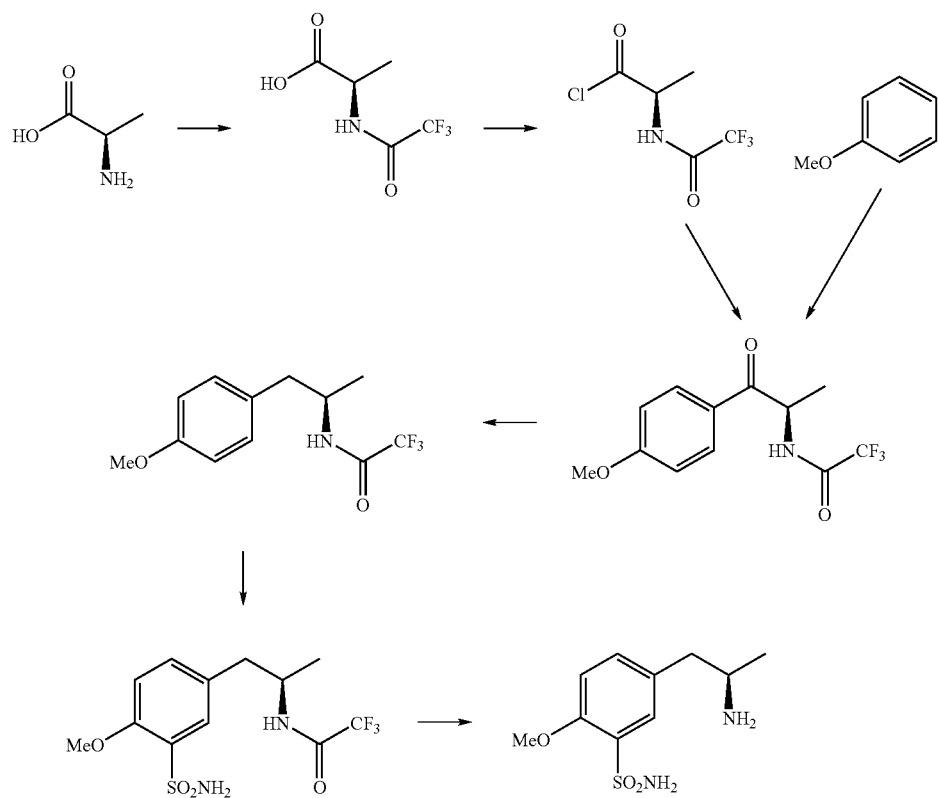

The invention claimed is:

1. A process for making (R)-5-(2-aminopropyl)-2-methoxybenzene sulphonamide comprising the following steps: a) protection of the amino group of D-alanine, b) reaction of the N-protected D-alanine with methoxybenzene to make 4'-methoxy-2-amino protected propiophenone, c) reduction of the oxo-group of the 4'-methoxy-2-amino protected propiophenone to make amino-protected 1-(4-methoxyphenyl) propane-2-amine, d) chlorosulphonation of the amino-protected 1-(4-methoxyphenyl)propane-2-amine and ammonolysis of the chlorosulphonyl group, and e) deprotecton of the amino group.

2. The process according to claim 1 wherein said protection in step (a) is carried out with ethyl trifluoroacetate.

3. The process according to claim 1 wherein a Lewis acid is added in step (b).

4. The process according to claim 3 wherein said Lewis acid is selected from the group consisting of bismuth, titanium, iron (III) or aluminum salt.

5. The process according to claim 3 wherein said Lewis acid is aluminum chloride.

6. The process according to claim 1 wherein step (c) is carried out with triethylsilane as a reducing agent.

7. The process according to claim 1 wherein step (d) is carried out with chlorosulphonic acid as a chlorosulphonation agent.

8. The process according to claim 1 wherein the reagent for ammonolysis of the chlorosulphonyl group comprises an aqueous solution of ammonia.

9. The process according to claim 1 wherein deprotection in step (e) is carried out with potassium carbonate.

10. A process for making tamsulosin or tamsulosin hydrochloride comprising: a) protection of the amino group of D-alanine. b) reaction of the N-protected D-alanine with methoxybenzene to make 4'-methoxy-2-amino protected propiophenone, c) reduction of the oxo-group of the 4'-methoxy-2-amino protected propiophenone to make amino- protected 1-(4-methoxyphenyl)propane-2-amine, d) chlorosulphonation of the amino-protected 1-(4-methoxyphenyl) propane-2-amine and subsequent ammonolysis of the chlorosulphonyl group, e) deprotection of the amino group, and f) o-ethoxy phenoxyethylation of the amino group to make tamsulosin.

11. The process according to claim 10 wherein said protection in step (a) is carried out with ethyl trifluoroacetate.

12. The process according to claim 10 wherein a Lewis acid is added in step (b).

13. The process according to claim 12 wherein said Lewis acid is selected from the group consisting of bismuth, titanium, iron (III) or alumimum salt.

14. The process according to claim 12 wherein said Lewis acid is iron (III) chloride.

15. The process according to claim 10 wherein step (c) is carried out with triethylsilane as a reducing agent.

16. The process according to claim 10 wherein step (d) is carried out with chlorosulphonic acid as a chlorosulphonation agent.

17. The process according to claim 10 wherein the reagent for ammonolysis of the chlorosulphonyl group comprises an aqueous solution of ammonia.

18. The process according to claim 10 wherein the deprotection in step (e) is carried out with potassium carbonate.

19. An intermediate derivative for use in the production of tamsulosin or pharmaceutically effective salts thereof which comprises (R)-1-(4-methoxy-3-sulphamoylphenyl)-2-trifluoroacetylaminopropane.

20. An intermediate derivative for use in the production of tamsulosin or pharmaceutically effective salts thereof which comprises (R)-1-(4-methoxy-3-sulphamoylphenyl)-2-trifluoroacetylamino-1-propanone.

21. The process according to claim 10 further comprising the step of treating the tamsulosin with ethanolic HCl to make tamsulosin hydrochloride.

* * * * *